United States Patent
West et al.

(10) Patent No.: US 7,744,937 B2
(45) Date of Patent: *Jun. 29, 2010

(54) CHEMOPROTECTANTS FROM CRUCIFER SEEDS AND SPROUTS

(75) Inventors: Leslie G. West, Glencoe, IL (US); George W. Haas, Mount Prospect, IL (US); Nathan Matusheski, Gurnee, IL (US)

(73) Assignee: Kraft Foods Global Brands LLC, Northfield, IL (US)

( * ) Notice: Subject to any disclaimer, the term of this patent is extended or adjusted under 35 U.S.C. 154(b) by 826 days.

This patent is subject to a terminal disclaimer.

(21) Appl. No.: 11/199,752

(22) Filed: Aug. 9, 2005

(65) Prior Publication Data

US 2007/0031581 A1 Feb. 8, 2007

(51) Int. Cl.
*A61K 36/31* (2006.01)
(52) U.S. Cl. ...................... 424/755; 424/776
(58) Field of Classification Search ............... None
See application file for complete search history.

(56) References Cited

U.S. PATENT DOCUMENTS

| | | | |
|---|---|---|---|
| 4,083,836 A | 4/1978 | Anjou et al. | |
| 5,043,178 A | 8/1991 | Gottesman, deceased et al. | |
| 5,077,071 A | 12/1991 | Strop | |
| 5,686,108 A | 11/1997 | Pusateri et al. | |
| 5,725,895 A | 3/1998 | Fahey et al. | |
| 5,882,646 A | 3/1999 | Pusateri et al. | |
| 5,968,505 A | 10/1999 | Fahey et al. | |
| 5,968,567 A | 10/1999 | Fahey et al. | |
| 6,086,936 A | 7/2000 | Wilson et al. | |
| 6,117,460 A | 9/2000 | Kortschack | |
| 6,177,122 B1 | 1/2001 | Fahey et al. | |
| 6,242,018 B1 | 6/2001 | Fahey et al. | |
| 6,348,220 B1 | 2/2002 | Ribnicky et al. | |
| 6,361,812 B1 | 3/2002 | Ekanayake et al. | |
| 6,436,450 B1 | 8/2002 | Omary et al. | |
| 6,521,818 B1 * | 2/2003 | Fahey | 800/306 |
| 6,737,441 B2 | 5/2004 | Fahey | |
| 6,812,248 B2 | 11/2004 | Zhang et al. | |
| 6,824,796 B2 | 11/2004 | Pusateri et al. | |
| 7,303,770 B2 | 12/2007 | Fahey et al. | |
| 7,371,419 B1 * | 5/2008 | West et al. | 424/776 |
| 7,402,569 B2 | 7/2008 | Fahey | |
| 7,407,986 B2 | 8/2008 | Gao et al. | |
| 2002/0015722 A1 | 2/2002 | Herzog et al. | |
| 2002/0090405 A1 | 7/2002 | Guthrie et al. | |
| 2002/0147155 A1 | 10/2002 | Foster et al. | |
| 2002/0151505 A1 | 10/2002 | Fahey | |
| 2003/0091518 A1 | 5/2003 | Pauly et al. | |
| 2003/0235634 A1 | 12/2003 | Pusateri et al. | |
| 2004/0001817 A1 | 1/2004 | Giampapa | |
| 2004/0052879 A1 | 3/2004 | Ravagnan et al. | |
| 2004/0133936 A1 | 7/2004 | Rossiter et al. | |
| 2005/0031768 A1 | 2/2005 | Sakai et al. | |
| 2005/0042347 A1 | 2/2005 | Bathurst et al. | |
| 2005/0055744 A1 | 3/2005 | Quiros et al. | |
| 2005/0123560 A1 | 6/2005 | Sinnott | |
| 2006/0003073 A1 | 1/2006 | Etzel et al. | |
| 2006/0020046 A1 | 1/2006 | Goralczyk et al. | |
| 2006/0127996 A1 | 6/2006 | Fahey | |
| 2007/0031581 A1 | 2/2007 | West et al. | |
| 2007/0033675 A1 | 2/2007 | Barten | |
| 2007/0190209 A1 | 8/2007 | Sinnott | |
| 2008/0107792 A1 | 5/2008 | Verhoeyen et al. | |

FOREIGN PATENT DOCUMENTS

| | | |
|---|---|---|
| DE | 19649952 | 6/1998 |
| DE | 102005033616 A1 | 1/2007 |
| EP | 0 006 654 A2 | 1/1980 |
| EP | 0668026 | 8/1995 |
| EP | 1100340 | 5/2001 |
| EP | 1 219 180 A1 | 7/2002 |
| EP | 1 752 052 A2 | 2/2007 |
| JP | 2005206495 A | 8/2005 |
| WO | WO 95/08275 | 3/1995 |
| WO | 19991007240 A1 | 2/1999 |
| WO | 19991020242 A1 | 4/1999 |
| WO | WO/00/01222 | 1/2000 |
| WO | 20001030604 A1 | 6/2000 |
| WO | 20001061163 A1 | 10/2000 |

(Continued)

OTHER PUBLICATIONS

See http://www.polylc.com/—accessed Nov. 2008.*

(Continued)

*Primary Examiner*—Susan C Hoffman
(74) *Attorney, Agent, or Firm*—Fitch, Even, Tabin & Flannery

(57) ABSTRACT

The present invention is directed to chemoprotectant precursor compositions provided from crucifer seeds and sprouts and methods for their preparation. Treatment of aqueous extracts from crucifer seeds or sprouts with adsorbents substantially increases the ratio of certain highly chemoprotectant precursor compounds (alkyl glucosinolates such as glucoraphanin, a.k.a. sulforaphane glucosinolate) to undesirable compounds such as indole glucosinolates (for example 4-hydroxyglucobrassicin). The method provides an extract which has a ratio of glucoraphanin to 4-hydroxyglucobrassicin of about 70 or greater. The resulting extract has improved color and odor and may be dried or used directly as an additive in a variety of foodstuffs.

7 Claims, 1 Drawing Sheet

FOREIGN PATENT DOCUMENTS

| | | |
|---|---|---|
| WO | 20011091764 A2 | 12/2001 |
| WO | 20021015722 A2 | 2/2002 |
| WO | 20031051313 A2 | 6/2003 |
| WO | 20041073418 A1 | 9/2004 |
| WO | 20051013722 A1 | 2/2005 |
| WO | 20061012213 A2 | 2/2006 |
| WO | 2006/102236 A1 | 9/2006 |
| WO | 20061102236 A1 | 9/2006 |
| WO | 20071094827 A1 | 8/2007 |

OTHER PUBLICATIONS

Letter from Richard Peet of Foley & Lardner LLP dated Apr. 18, 2008 to James P. Krueger of Fitch, Even, Tabin & Flannery regarding U.S. Patent Application Publication No. 2007/0031581 A1, (1 page).

Cecil H. VanEtten, Clara E. McGrew, and Melvin E. Daxenbichler, "Glucosinolate Determination in Cruciferous Seeds and Meals by Measurement of Enzymatically Released Glucose," Journal of Agricultural and Food Chemistry, vol. 22, No. 3, 1974, pp. 483-487.

Fahey J.W. et al., "Separation and Purification of Glucosinolates From Crude Plant Homogenates By High-Speed Counter-Current Chromatography." Journal of Chromatography A, vol. 996, No. 1-2, May 2003, pp. 85-93.

Hansen M. et al., "Glucosinolates in Broccoli Stored Under Controlled Atmosphere." Journal of the American Society of Horticultural Science, vol. 120, No. 6, 1995, pp. 1069-1074.

Kushad Mosbah M. et al., "Variation of Glucosinolates in Vegetable Crops of Brassica Oleracea." Journal of Agricultural and Food Chemistry, vol. 47, No. 4, Apr. 1999, pp. 1541-1548.

Lewis J. et al., "Glucosinolate Content of Brassica Vegetables: Analysis of Twenty-Four Cultivars of Calabrese." Food Chemistry, vol. 25, No. 4, 1987, pp. 259-268.

Pereira F. M. V. et al., "Influence of Temperature and Ontogeny of the Levels of Glucosinolates in Broccoli Sprouts and Their Effect on the Induction of Mammalian Phase 2 Enzymes." Journal of Agricultural and Food Chemistry, vol. 50, No. 21, 2002, pp. 6239-6244.

Vallejo F. et al., "Potential Bioactive Compounds in Health Promotion From Broccoli Cultivars Grown in Spain." Journal of the Science of Food and Agriculture, vol. 82, No. 11, Sep. 2002, pp. 1293-1297.

Vallejo F. et al., "Total and Individual Glucosinolate Contents in inflorescences of Eight Broccoli Cultivars Grown Under Various Climatic and Fertilisation Conditions." Journal of the Science of Food and Agriculture, vol. 83, No. 4, Mar. 2006, pp. 307-313.

West L.G. et al., "Glucoraphanin and 4-hydroxyglucobrassicin Contents in Seeds of 59 Cultivars of Broccoli, Raab, Kohlrabi, Radish, Cauliflower, Brussels Sprouts, Kale, and Cabbage." Journal of Agricultural and Food Chemistry, vol. 52, No. 4, 2004, pp. 916-926.

EP Search Report, EP 05106785 (4 pages), 2005.

Cheftel, "Hautes Pressions, Inactivation Microbienne et Conservation des Aliments", C. R. Acad. Agric. Fr., 1995, 81(1), pp. 13-38.

Mor-Mur et al., "High Pressure Processing Applied to Cooked Sausage Manufacture: Physical Properties and Sensor Analysis", Meat Science, 2003, 65, pp. 1187-1191.

West et al., "Single Column Approach for the Liquid Chromatographic Separation of Polar and Non-Polar Glucosinolates from Broccoli Sprouts and Seeds", Journal of Chromatography A. 2002, 966, pp. 227-232.

Birthe Bjerg et al., "Isolation Of Intact Glucosinolates By Column Chromatography And Determination Of Their Purity", Glucosinolates in Rapeseeds: Analytical Aspects, Oct. 1986, pp. 59-75, Martinus Nijhoff a member of the Kluwer Academic Publishers Group, Belgium.

Rita Cortesi, et al., "Hydroxy Propyl Methyl Cellulose Phthalate (HPMCP) Microparticles For Enteric Delivery of Glucosinolate Derived Products From Cruciferous Vegetable", Minerva Biotecnologica, vol. 12, No. 4, 2000, pp. 293-300.

Frank Desilva et al., "Some Like It Hot, Some Like It Cold". Published in Water Quality Products Magazine, Aug. 2000, 4 pages.

M.S. Epstein et al., "Determination of Phosphorus in Copper-Based Alloys Using Ion-Exchange Chromatography and Direct-Current Plasma Emission Spectrometry". Analytical Chemistry, 1987, 59, 2872-2876.

Jed W. Fahey et al., "The Chemical Diversity And Distribution of Glucosinolates And Isothiocyanates Among Plants", Phytochemistry, 2001, vol. 56, pp. 5-51.

A. Bryan Hanley et al., "Improved Isolation Of Glucobrassicin And Other Glucosinolates", Journal of Science and Food Agriculture, 1983, vol. 34, pp. 869-873.

Mosbah M. Kushad et al., "Variation of Gluconsinolates in Vegetable Crops of Brassica oleracea". J. Agricultrual Food Chemistry. 1999. 47, 1541-1548. Simone Rochfort et al., the Isolation and Purification of Glucoraphanin From Broccoli Seeds by Solid Phase.

Simone Rochfort et al., "The Isolation and Purification Of Glucoraphanin From Broccoli Seeds By Solid Phase Extraction And Preparative High Performance Liquid Chromatography" Journal of Chromatography A, 2006, vol. 1120, pp. 205-210. incomplete copy provided.

Lijiang Song et al., "Purification Of Major Glucosinolates From Brassicaceae Seeds And Preparation Of Isothiocyanate And Amine Metabolites", Journal of Science and Food Agriculture; 2006, vol. 86, pp. 1271-1280.

Anna M. Szmigielska et al., "Determination of Glucosinolates in Canola Seeds Using Anion Exchange Membrane Extraction Combined with the High-Pressure Liquid Chromatography Detection" Journal of Agricultural Food and Chemical, 2000, vol. 48(10), pp. 4487-4491.

John K. Troyer et al., "Analysis Of Glucosinolates From Broccoli And Other Cruciferous Vegetables By Hydrophilic Interaction Liquid Chromatography", Journal of Chromatography A, 2001, vol. 919, pp. 299-304.

* cited by examiner

Fig. 1

Seeds

↓ pulverize (mills, grinders, blenders)

↓ remove hexane-soluble lipids (recycle hexane after recovering lipids for further processing)

Defatted Seeds or Fresh Sprouts

↓ extract glucoraphanin with hot water (sprouts require chopping in the presence of hot water)

↓ clarify extract by filtration and/or centrifugation (recover solids for further processing)

↓ purify extract with activated charcoal

↓ clarify purified extract by filtration and/or centrifugation

↓ further purify extract by ultrafiltration to remove higher MW impurities if desired ↓ dry clarified/purified extract/ultrafiltrate if desired Chemoprotectant Compounds

CHEMOPROTECTANTS FROM CRUCIFER SEEDS AND SPROUTS

The present invention relates to chemoprotective compounds and method for producing chemoprotective compounds which may be incorporated into a variety of food products. More specifically, an extraction method is provided that is effective for providing an extract having a high ratio of chemoprotective compounds to less desirable compounds while providing a high yield of chemoprotective compounds. Enhanced yields and ratios of chemoprotective compounds are provided by an aqueous extraction method used in combination with adsorbents.

BACKGROUND

It is generally agreed that diet plays a large role in controlling the risk of developing cancers and that increased consumption of fruits and vegetables may reduce cancer incidences in humans. The presence of certain minor chemical components in plants may provide a major protection mechanism when delivered to mammalian cells.

Cruciferious vegetables contain phytochemical precursors to potent chemoprotectants especially glucoraphanin and its associated conversion product sulforaphane, that when delivered to mammalian cells trigger carcinogen detoxification mechanisms. In addition to reducing the risk of getting certain cancers, glucoraphanin through its bioactive conversion product sulforphane has recently been shown effective in destroying the organism responsible for causing the majority of stomach ulcers and may provide novel approaches for reducing the risk of developing cardiovascular and ocular diseases. Efforts are being undertaken to gain approval for making label claims on food products either naturally high in these agents or for foods containing added crucifer chemoprotectants. Products containing chemoprotectant additives, although without claims, are already on the market.

Cruciferous vegetables also contain other compounds, such as indole glucosinolates, which are problematic for maintaining good health. Not only are these compounds weak inducers of the carcinogen detoxification system, but also they can induce systems which may bioactivate certain procarcinogens. In addition, the breakdown products of indole glucosinolates formed in the stomach during digestion may act in a similar manner to dioxin, a very potent toxin. Therefore, it is advantageous to produce glucoraphanin-containing preparations containing as little residual indole glucosinolates, or other adverse compounds, as possible.

Several patents describe the development of highly chemoprotecant crucifer germplasm with a significantly improved ratio of glucoraphanin to indole glucosinolates (increasing the ratio from about 0.2 to ~30). See, e.g., U.S. Pat. Nos. 6,521,818, 6,242,018, 6,177,122, 5,968,567, 5,968,505 and 5,725,895; however, developing the germplasm from laboratory to field trials to market will require considerable time, upwards of up to 5 years, and with no guarantee of success. Hence, there is a need to provide alternative methods for producing high yields of glucoraphanin with a high ratio of glucoraphanin to indole glucosinolates.

SUMMARY

The present invention is directed to chemoprotectant precursor compositions provided from crucifer seeds and sprouts and methods for their preparation. Treatment of aqueous extracts from crucifer seeds or sprouts with adsorbents substantially increases the ratio of certain highly chemoprotectant precursor compounds (alkyl glucosinolates such as glucoraphanin, a.k.a. sulforaphane glucosinolate) to undesirable compounds such as indole glucosinolates (for example 4-hydroxyglucobrassicin). The method provides an extract which has a ratio of glucoraphanin to 4-hydroxyglucobrassicin of about 70 or greater. The resulting extract has improved color and odor and may be dried or used directly as an additive in a variety of foodstuffs.

A method is provided for extracting chemoprotectants precursors from crucifer seeds or sprouts. Generally, the method includes forming an aqueous extract of crucifer seeds or sprouts. The aqueous extract is contacted with an adsorbent. The aqueous extract is separated from the adsorbent to provide a chemoprotectant enhanced extract. The method is effective for providing a chemoprotectant enhanced extract having a ratio of a number of alkyl glucosinolates, especially glucoraphanin to indole glucosinolates, specifically 4-hydroxyglucobrassicin of about 30 to about 1000 or greater, preferably about 100 to about 1000.

Crucifer vegetables have been identified as a good source of chemoprotectant precursor phytochemicals. Crucifer seeds and sprouts have been found to be an especially good source of chemoprotectant precursors. Crucifer seeds or sprouts which are especially useful include broccoli, kale, collard, curly kale, marrowstem kale, thousand head kale, Chinese kale, cauliflower, Portuguese kale, Brussels sprouts, kohlrabi, Jersey kale, savoy cabbage, collards, borecole, radish, and the like as well as mixtures thereof. In a very important aspect, crucifer seeds or seeds and sprouts of broccoli are utilized.

When crucifer seeds are used as a starting material, they may be used directly or may be processed prior to aqueous extraction. In one aspect, crucifer seeds may be defatted prior to forming an aqueous extract using known defatting procedures. For example, West, L. et al., *J Arc. Food Chem.* 2004, 52, 916-926, which is incorporated herein by reference. In another aspect, crucifer seeds may be ground, pulverized or blended prior to addition of aqueous extract or simultaneously with the addition of an aqueous extract.

Extraction of seed or sprouts may be conducted with water or water containing an organic solvent, such as ethyl alcohol. In another alternative aspect, an aqueous extract of crucifer seeds or sprouts is formed by contacting crucifer seeds or sprouts with water having a temperature of 60 to 110° C. for at least 5 minutes.

The aqueous extract of seeds or sprouts is contacted with an adsorbent. The aqueous extract may be separated from cellular materials and be free of seed and sprout cellular materials. Alternatively, the aqueous extract with cellular materials may be contacted directly with adsorbents. Adsorbents which may be utilized include activated carbon, silica, chemically-modified silica, bleaching clay and the like as well as and mixtures thereof. In a very important aspect, the adsorbent is activated carbon. Generally, about 1 to about 20 weight percent adsorbent is mixed with the aqueous extract. In a very important aspect, about 8 to about 12 weight percent adsorbent is mixed with the aqueous extract.

In another aspect, the aqueous extract of seeds or sprouts is added to a column containing adsorbent materials. In this aspect, column processing is effective for providing an extract having a ratio of alkyl glucosinolates, especially glucoraphanin to indole glucosinolates, specifically 4-hydroxyglucobrassicin, of about 30 to about 1000 or greater, preferably about 100 to about 1000.

In another aspect, food products are provided that include the chemoprotectant or chemoprotectant precursor enhanced extract. The extract may be incorporated directly into food products or dried, cooled, frozen or freeze-dried and then incorporated into the food products. Food product into which the extract may be incorporated include food supplements, drinks, shakes, baked goods, teas, soups, cereals, pills, tablets, salads, sandwiches, granolas, salad dressings, sauces, coffee, cheeses, yogurts, energy bars and the like as well as mixtures thereof. In this aspect, the food product may contain an amount of extract effective for providing the food product with 0.003 weight percent to 0.05 weight percent glucoraphanin.

BRIEF DESCRIPTION OF THE FIGURE

FIG. 1 provides a general description of methods for extracting chemoprotectant compounds from crucifer seeds or sprouts.

DETAILED DESCRIPTION

As shown in FIG. 1, crucifer seeds and/or sprouts may be processed in a number of different ways. An aqueous extract of the seeds or sprouts may be formed and then mixed with adsorbents or applied to an adsorbent-containing column. Alternatively, the seeds or sprouts may be mixed directly with an aqueous extract and adsorbents. Seeds or sprouts may extracted with blending, homogenizing. or pulverizing using known methods.

As used herein "chemoprotectants" and "chemoprotective compounds" refers to agents of plant origin that are effective for reducing the susceptibility of mammals to the toxic and neoplastic effects of carcinogens. Chemoprotectant "precursors" refer to agents which give rise to chemoprotectants by enzymatic and/or chemical means. Talalay, P. et al, *J. Nutr* 2001, 131 (11 Suppl), 30275-30335. Examples of such chemoprotectant precursors include alkyl glucosinolates, such as glucoraphanin.

As used herein "aqueous extract" means extracts prepared with 100% water or up to 25% addition of an organic solvent, such as ethyl alcohol.

Other methods which may be used to selectively concentrate chemoprotectants and chemoprotectant precursors include: preparative liquid chromatography, membrane ultrafiltration, selective precipitation, preparative electrophoresis and preparative counter current distribution techniques. Troyer, J. et al., *J. Chromatogr. A* 2001, 919, 299-304; West, L. et al. *J. Chromatogr. A* 2002, 966, 227-232; Fahey, J. et al. *J. Chromatogr. A* 2003, 966, 85-93; and Iori, R., Patent Application B098A 000425 1998. In another alternative, to further purify extracts based on molecular weight, chemoprotectant precursor enhanced extract may be ultrafiltered through >500 MWCO (molecular weight cut-off) filters.

Crucifer Seeds and Sprouts

Crucifer seed and sprouts are useful starting materials. The ratio of glucoraphanin to indole glucosinolates is naturally higher in seeds (average of ~4, with a range of 0.4 to 11) than vegetative tissue. Seeds and sprouts are preferred as a starting material since they have higher amounts of glucoraphanin as compared to mature plants. Seed and sprouts are easier to process and less expensive than mature plants.

Sprouts suitable as sources of cancer chemoprotectants are generally cruciferous sprouts (family Brassicaceae). Preferably the sprouts are *Brassica oleracea* ssp. selected from the group of varieties consisting of acephala (kale, collard, wild cabbage, curly kale), medullosa (marrowstem kale) ramose (thousand head kale), alboglabra (Chinese kale), botrytis (cauliflower, sprouting broccoli), costata (Portuguese kale), gemmifera (Brussels sprouts), gogylodes (kohlrabi), italica (broccoli), palmifolia (Jersey kale), sabauda (savoy cabbage), sabellica (collards), and selensia (borecole), among others. Numerous methods for the cultivation of sprouts are known, as exemplified by U.S. Pat. Nos. 3,733,745, 3,643,376, 3,945, 148, 4,130,964, 4,292,769 and 4,086,725 which are all incorporated herein by reference. Sprouts may be prepared in commercial sprouters, providing water (misting 6 times/day) and light (10 hours/day) over a 5-day period.

Particularly useful broccoli cultivars to be used in the claimed method are Saga, DeCicco, Everest, Emerald City, Packman, Corvet, Dandy, Early, Emperor, Mariner, Green Comet, Green Valiant, Arcadia, Calabrese Caravel, Chancellor, Citation, Cruiser, Early Purple Sprouting Red Arrow, Eureka, Excelsior, Galleon, Ginga, Goliath, Green Duke, Greenblet, Italian Sprouting, Late Purple Sprouting, Late Winter Sprouting, White Star, Legend, Leprechaun, Marathon, Mariner, Minaret (Romanesco), Paragon, Patriot, Premium Crop, Rapine (Spring Raab), Rosalind, Salade (Fall Raab), Samurai, Shogun, Sprinter, Sultan, Taiko, Trixie, San Miguel, Arcadia, Gypsy, Everest, Patron, Southern Comet, Green Comet, Destiny, Climax and Pirate. However, many other broccoli cultivars are suitable.

Adsorbents

Crucifers seed or sprouts or aqueous extracts of crucifer seed or sprouts may be mixed directly with adsorbents in batch mode, semi-continuous mode or continuous mode (e.g. using an adsorbent column). As used herein, adsorbents refer to compounds that are effective for preferentially adsorbing indole glucosinolates over alkyl glucosinolates. Useful adsorbents include activated carbon, including Norit A and Darco 12-20 mesh granular. Additional adsorbents demonstrating some effectiveness include silica, chemically-modified silica (so called C-18 loaded), and bleaching clay (used routinely in vegetable oil processing). Adsorbents found ineffective included alumina (neutral, acidic and basic) and Fuller's earth (montmorillonite).

Processing of Extracts

Chemoprotectant precursor enhanced extracts of crucifers seeds may be incorporated into a variety of foodstuffs. The extract may be dried, cooled, frozen or freeze-dried using known methods. Alternatively, extracts may be further processed, for example with membrane-processing or dialysis to remove high molecular weight compounds such as proteins and polysaccharides.

EXAMPLES

Example 1

Batch Processing of Broccoli Seeds

A 30 ml sample of aqueous extract from 1 g of pulverized defatted broccoli seed (var.Gypsy) was treated with 100 mg of activated carbon (Darco G-60) 12-20 mesh by boiling for 1 min. in 30 ml of water followed by filtration to remove spent adsorbent and provide an aqueous extract. The initial ratio of glucoraphanin/4-hydroxglucobrassicin of ~11 in the initial seed was increased to ~70 in the treated matter. Loss of glucoraphanin was ~4% as determined by high performance liquid chromatography (HPLC), West, L. et al., *J. Chromatogr. A* 2002, 966, 227-232.

Example 2

Column Processing of Broccoli Seeds

A 30 ml sample of aqueous extract from 1 g of pulverized defatted broccoli seed (var Gypsy) was passed down a column containing 1000 mg of graphitized carbon black. The initial ratio of glucoraphanin/4-hydroxyglucobrassicin of ~11 in the initial seed was increased to >1000. Loss of glucoraphanin was ~13% as determined by HPLC.

Example 3

Boiling Water Processing of Broccoli Seeds

A 100 mg portion of activated carbon (Darco G-60) was admixed with 1 g of pulverized defatted broccoli seed (var. Gypsy) and extracted in boiling water followed by centrifugation to remove particulates. The initial ratio of glucoraphanin/4-hydroxyglucobrassicin of ~11 was increased to ~30. Loss of glucoraphanin was ~2% as determined by HPLC.

Example 4

Processing of Broccoli Seeds with Ultrafiltration

A 200 g. portion of pulverized and defatted (hexane extractable lipids) broccoli seed (var. Premium Crop) was added to 2 L of boiling water. After 5 min. at boiling water temperature, the mixture was filtered to remove residual plant material and the aqueous extract was treated with 20 g. of activated carbon (Darco G-60) by boiling for ~1 min. followed by centrifugation and filtration to remove spent adsorbent. The clarified extract was ultrafiltered using a 3000 MWCO membrane all the while retaining the ultrafiltrate. After drying, the light tan in color powder was analyzed by HPLC and found to contain over 30% glucoraphanin by weight and a glucoraphanin/4-hydroxyglucobrassicin ratio of greater than 1000.

Example 5

Processing of Broccoli Sprouts with Blending and Ultrafiltration

A 500 g. sample of ~5 day old whole fresh broccoli sprouts (sprouted from var. Premium Crop) were added to 2 L of boiling water. After 10 min. at boiling water temperature, the mixture was transferred to a blender operating at high speed to disrupt the plant tissue for the purpose of further releasing glucoraphanin. After filtration to remove the residual plant material, the aqueous extract was treated with 20 g. of activated carbon (Darco G-60) by boiling for ~1 min. followed by centrifugation and filtration to remove spent adsorbent. The clarified extract was ultrafiltered using a 3000 MWCO membrane all the while retaining the ultrafiltrate. After drying, the white in color powder was analyzed by HPLC and found to contain over 10% glucoraphanin by weight and a glucoraphanin/4-hydroxyglucobrassicin ratio of greater than 1000.

What is claimed is:

1. A method for extracting chemoprotectant precursors comprising:
   forming an aqueous extract of broccoli seeds or sprouts;
   contacting the aqueous extract with about 8 to about 12 weight percent of activated carbon; and
   separating the activated carbon from the aqueous extract to provide a chemoprotectant precursor enhanced extract,
   the method effective for providing a chemoprotectant precursor enhanced extract having a ratio of a number of alkyl glucosinolates to indole glucosinolates of at least about 30.

2. The method of claim 1, wherein the alkyl glucosinolates are glucoraphanin.

3. The method of claim 1, wherein the indole glucosinolates are 4-hydroxyglucobrassicin.

4. The method of claim 1, wherein the ratio of number of alkyl glucosinolates to indole glucosinolates is about 30 to about 1000.

5. The method of claim 1, wherein the ratio of alkyl glucosinolates to indole glucosinolates is about 1000 or greater.

6. The method of claim 1, wherein the broccoli seeds are defatted prior to forming an aqueous extract.

7. The method of claim 1, wherein the aqueous extract of broccoli seeds or sprouts is formed by contacting the broccoli seeds or sprouts with water having a temperature of about 60° to 110° C. for at least about 5 minutes.

* * * * *